United States Patent
Haham et al.

(10) Patent No.: US 10,182,733 B2
(45) Date of Patent: Jan. 22, 2019

(54) MULTIPLE LED SENSORS ON A FIBEROPTIC CABLE USED AS A CATHETER

(71) Applicant: BIOSENSE WEBSTER (ISRAEL) LTD., Yokeneam (IL)

(72) Inventors: Moti Shor Haham, Kiryat Ono (IL); Ronen Krupnik, Karmiel (IL); Genady Kagan, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 431 days.

(21) Appl. No.: 14/203,645

(22) Filed: Mar. 11, 2014

(65) Prior Publication Data
US 2015/0257665 A1    Sep. 17, 2015

(51) Int. Cl.

| A61B 5/04 | (2006.01) |
|---|---|
| A61B 5/042 | (2006.01) |
| A61B 5/00 | (2006.01) |
| A61B 5/0428 | (2006.01) |
| A61B 18/14 | (2006.01) |
| A61B 17/32 | (2006.01) |
| A61B 18/20 | (2006.01) |

(Continued)

(52) U.S. Cl.
CPC ............ *A61B 5/042* (2013.01); *A61B 5/0084* (2013.01); *A61B 5/0422* (2013.01); *A61B 5/04282* (2013.01); *A61B 5/7225* (2013.01); *A61B 5/7228* (2013.01); *A61B 5/6852* (2013.01); *A61B 17/320068* (2013.01); *A61B 18/1492* (2013.01); *A61B 18/20* (2013.01); *A61B 2018/00011* (2013.01); *A61B 2018/00577* (2013.01); *A61B 2018/00815* (2013.01); *A61B 2018/00821* (2013.01); *A61B 2018/00875* (2013.01); *A61B 2034/2051* (2016.02); *A61B 2218/002* (2013.01); *A61B 2562/223* (2013.01)

(58) Field of Classification Search
CPC ............................................. A61N 2001/086
See application file for complete search history.

(56) References Cited

U.S. PATENT DOCUMENTS

| 5,546,951 A | 8/1996 | Ben Haim |
| 6,226,542 B1 | 5/2001 | Reisfeld |

(Continued)

FOREIGN PATENT DOCUMENTS

| EP | 2248480 A1 | 11/2010 |
| WO | WO 96/05768 A1 | 2/1996 |
| WO | WO 01/75359 | 10/2001 |

OTHER PUBLICATIONS

European Search Report dated Aug. 24, 2015 for corresponding Application No. EP15158390.3.

*Primary Examiner* — Luther G Behringer
(74) *Attorney, Agent, or Firm* — Louis J. Capezzuto

(57) ABSTRACT

A fiberoptic waveguide connectable to an optical receiver, and a plurality of electro-optical elements optically coupled to the waveguide. The electro-optical elements each have a first electrode with a first polarity, and a second electrode with a second polarity. A light-emitting diode is linked to the first electrode and configured for illuminating the waveguide responsively to an electrical potential between the first electrode and the second electrode at a respective wavelength. The waveguide may be incorporated into a catheter for insertion into a subject, such as a cardiac catheter.

16 Claims, 4 Drawing Sheets

(51) Int. Cl.
   *A61B 18/00*     (2006.01)
   *A61B 34/20*     (2016.01)

(56) References Cited

U.S. PATENT DOCUMENTS

| | | | |
|---|---|---|---|
| 6,301,496 | B1 | 10/2001 | Reisfeld |
| 6,690,963 | B2 | 2/2004 | Ben Haim |
| 6,718,203 | B2 * | 4/2004 | Weiner ............ A61N 1/056 607/2 |
| 6,814,733 | B2 | 11/2004 | Schwartz |
| 6,892,091 | B1 | 5/2005 | Ben Haim |
| 6,980,848 | B2 | 12/2005 | Helfer |
| 6,997,924 | B2 | 2/2006 | Schwartz |
| 7,156,816 | B2 | 1/2007 | Schwartz |
| 7,519,407 | B2 | 4/2009 | Axelrod |
| 7,536,218 | B2 | 5/2009 | Govari |
| 7,756,576 | B2 | 7/2010 | Levin |
| 2002/0116029 | A1 | 8/2002 | Miller et al. |
| 2002/0147470 | A1 * | 10/2002 | Weiner ............ A61N 1/056 607/9 |
| 2007/0016007 | A1 | 1/2007 | Govari |
| 2007/0060832 | A1 | 3/2007 | Levin |
| 2009/0005773 | A1 * | 1/2009 | Beeckler ......... A61B 5/14542 606/41 |
| 2009/0131930 | A1 * | 5/2009 | Gelbart ........... A61B 18/1492 606/41 |
| 2013/0123600 | A1 * | 5/2013 | Tcheng ............ A61B 5/0478 600/378 |

* cited by examiner

MULTIPLE LED SENSORS ON A FIBEROPTIC CABLE USED AS A CATHETER

BACKGROUND OF THE INVENTION

Field of the Invention

This invention relates to cardiac physiology. More particularly, this invention relates to the evaluation of electrical propagation in the heart.

Description of the Related Art

Cardiac arrhythmias such as atrial fibrillation are an important cause of morbidity and death. Commonly assigned U.S. Pat. Nos. 5,546,951, and 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

SUMMARY OF THE INVENTION

Electrical activity at a point in the heart is now often measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

There is provided according to embodiments of the invention an apparatus, including a fiberoptic waveguide connectable to an optical receiver, and a plurality of electro-optical elements optically coupled to the waveguide. The electro-optical elements each have a first electrode with a first polarity and a second electrode with a second polarity. A light-emitting diode is linked to the first electrode and configured for illuminating the waveguide responsively to an electrical potential between the first electrode and the second electrode at a respective wavelength.

According to one aspect of the apparatus, the second electrodes of the electro-optical elements are connected in common.

According to a further aspect of the apparatus, the electro-optical elements further comprise respective transmissive optical elements, and the waveguide includes a core and a cladding layer formed coaxially about the core. The cladding layer has optically transparent gaps formed therein, and the transmissive optical elements overlie the gaps.

In yet another aspect of the apparatus, an optic terminator is disposed in the waveguide.

According to still another aspect of the apparatus, the electro-optical elements further comprise an analog-to-digital converter linked to the first electrode and to the light-emitting diode.

According to an additional aspect of the apparatus, the electro-optical elements further comprise an amplifier linked to the first electrode and to the analog-to-digital converter.

Another aspect of the apparatus includes a third electrode and a wire connected to the third electrode for exchanging electrical signals between the third electrode and a source.

In one aspect of the apparatus, the waveguide is coaxially disposed within a probe.

According to a further aspect of the apparatus, the first electrode and the second electrode are spaced apart from the light-emitting diode at a distance measured from an exterior of the waveguide to an outer wall of the probe.

There is further provided according to embodiments of the invention a method, which is carried out by inserting a probe into a heart of a living subject to contact a target, and connecting the probe to an optical receiver. The probe includes a fiberoptic waveguide and a plurality of electro-optical elements optically coupled to the waveguide, the electro-optical elements each having a first electrode at a first polarity, a second electrode at a second polarity and a light-emitting diode linked to the first electrode. The method is further carried out by detecting respective electrical potentials at the target with the electro-optical elements, and communicating optical signals from the electro-optical elements to the optical receiver responsively to the respective electrical potentials by illuminating the waveguide at respective wavelengths.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

The terms "link", "links", "couple" and "couples" are intended to mean either an indirect or direct connection. Thus, if a first device couples to a second device, that connection may be through a direct connection, or through an indirect connection via other devices and connections.

Figure 1:
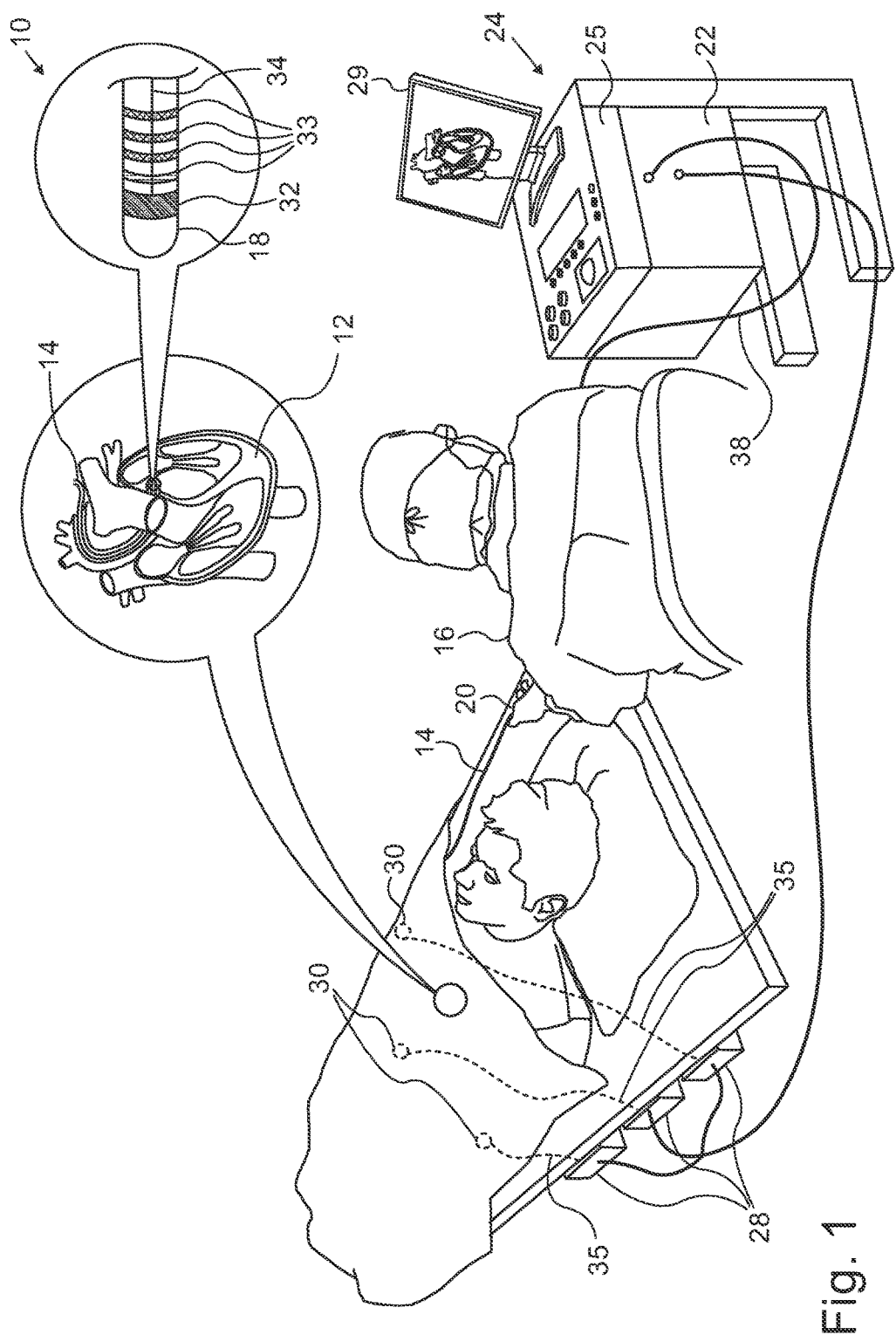
FIG. 1 is a pictorial illustration of a system for performing medical procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at a target site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 may comprise position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 may link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 may include a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site may be provided.

Figure 2:
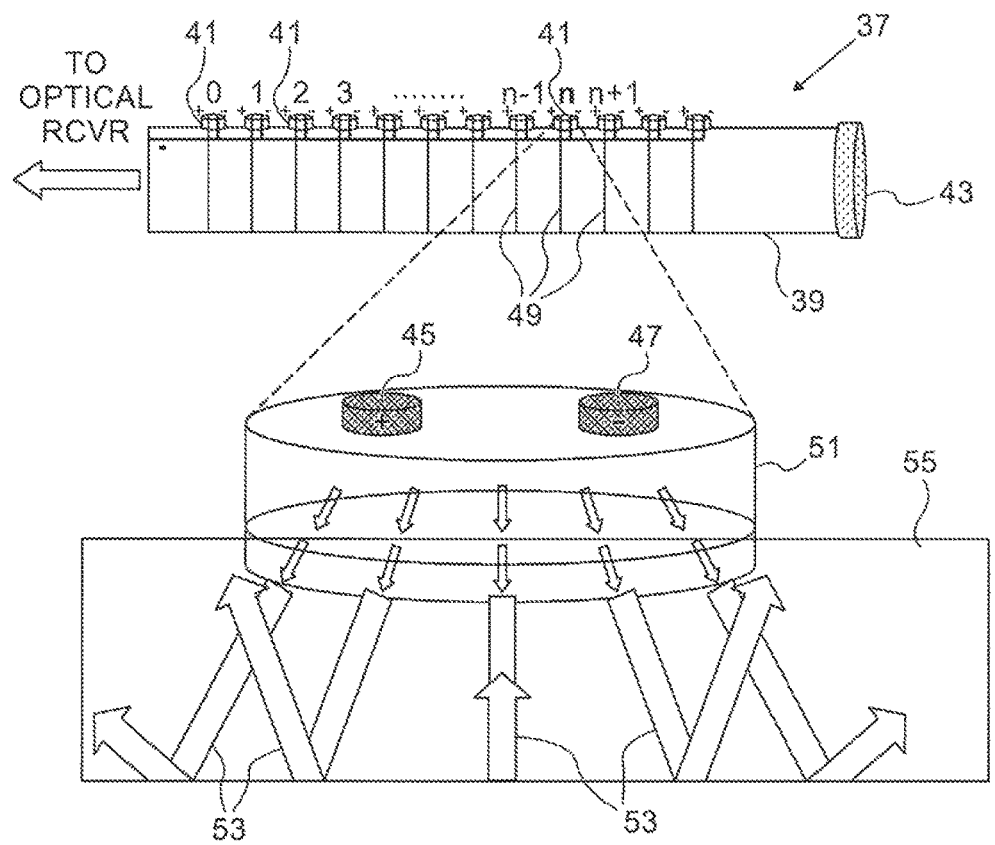
FIG. 2 is a schematic diagram of a catheter, in accordance with an embodiment of the invention.

Reference is now made to FIG. 2, which is a schematic diagram of a catheter 37, in accordance with an embodiment of the invention. The catheter 37 comprises a fiberoptic cable 39 having multiple sensor assemblies 41 mounted along its distal portion, and an optical terminator 43. The fiberoptic cable 39 may consist of a single multimode optical fiber comprising a core and cladding layer. Gaps, defects or plugs are formed in the cladding layer beneath the assemblies 41 and are sufficiently optically transparent to permit passage of light produced in the assemblies 41 into the core. Each of the assemblies 41 has a positive electrode 45 and a negative electrode 47. The negative electrode 47 of all the assemblies 41 are connected in common. The positive electrodes 45 are connected to respective conductive rings 49. The conductive rings 49 encircle the exterior of the fiberoptic cable 39. Signals reflecting the electrical potential of the conductive rings 49 and the positive electrode 45 are communicated from the positive electrodes 45 to a respective light-emitting diode LED 51 that is disposed in each of the assemblies 41. Light emitted by the LED 51, represented by arrows 53, propagates within interior 55 of the fiberoptic cable 39 toward an optical receiver (not shown).

Figure 3:
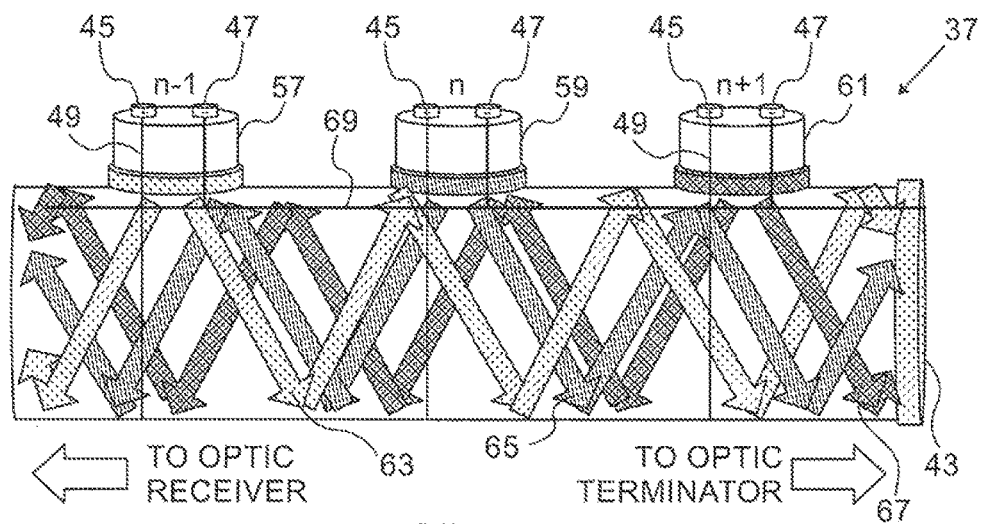
FIG. 3 is a detailed partial schematic view of the catheter shown in FIG. 2, in accordance with an embodiment of the invention.

Reference is now made to FIG. 3, which is a detailed partial schematic view of the catheter 37 (FIG. 2) in accordance with an embodiment of the invention. The assemblies 41 (FIG. 2) are shown as assemblies 57, 59, 61, each emitting light at a respective wavelength, which can vary from 450-1650 nm, represented by arrows 63, 65, 67, each having a unique hatched pattern. A common connection 69 links the negative electrodes 47. An optical receiver (not shown) coupled to the proximal end of the catheter 37 discriminates the optical signals produced by the assemblies 57, 59, 61 using methods known in the art of wavelength division multiplexing. The optical signals are converted to analog or digital electrical signals and processed conventionally in the console 24 (FIG. 1).

Figure 4:
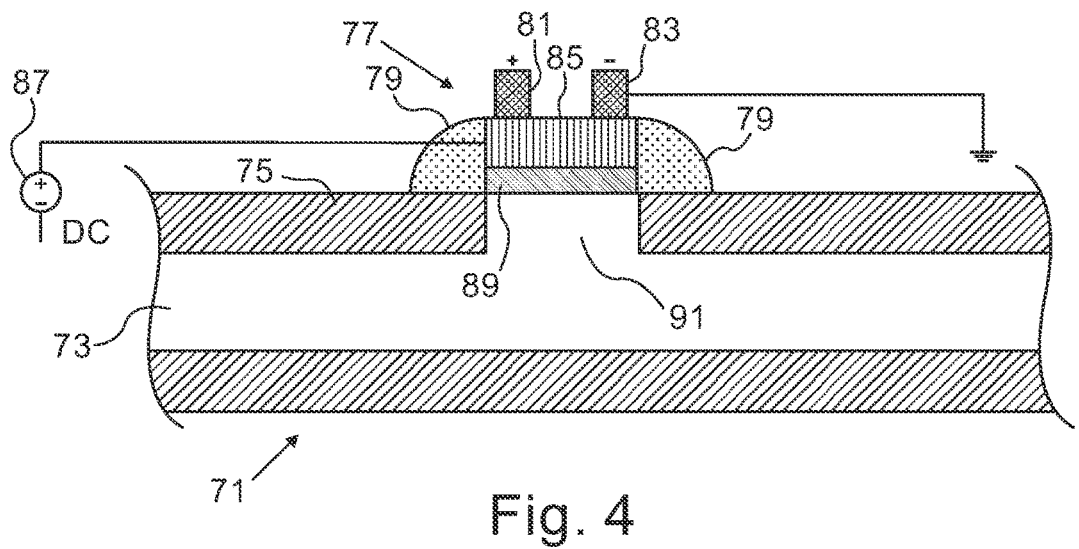
FIG. 4 is a schematic sectional view of a portion of a catheter, in accordance with an embodiment of the invention.

Reference is now made to FIG. 4, which is a schematic sectional view of a portion of a catheter, in accordance with an embodiment of the invention. An optical fiber 71 has a core 73 and a cladding layer 75. An electro-optical assembly 77 is secured on the exterior of the optical fiber 71 by glue 79. The electro-optical assembly 77 comprises electrodes 81, 83, A package 85 contains an LED, which is powered by a direct current source 87 and is connected to the electrode 81. The electrode 83 is connected to ground.

LED optics 89 comprise a transmissive element such as a lens. The optics 89 overly a gap 91 formed in the cladding layer 75, enabling light emitted through the optics 89 to enter the core 73.

Figure 5:
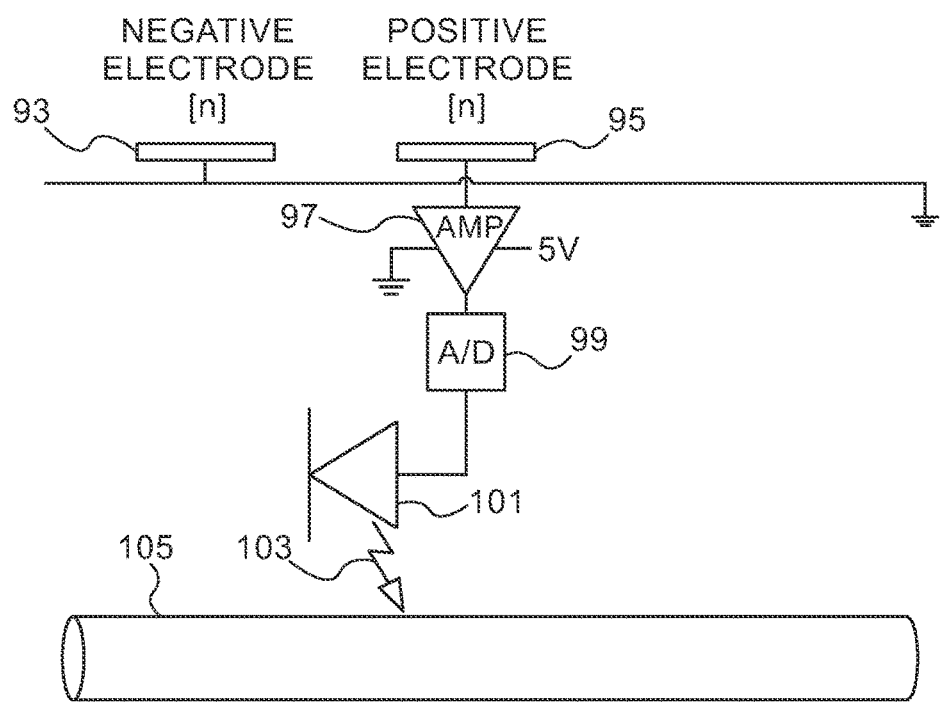
FIG. 5 is an electro-optical schematic of an assembly of the catheter shown in FIG. 2, in accordance with an embodiment of the invention.

Reference is now made to FIG. 5, which is an electro-optical schematic of one of the assemblies 41 (FIG. 2), in accordance with an embodiment of the invention. Negative electrode 93 is connected to ground. Positive electrode 95 is an input to an operational amplifier 97, whose output is digitized in an analog-to-digital converter 99 (A/D). A light-emitting diode 101 is connected to the output of the analog-to-digital converter 99. Light 103 is emitted by the light-emitting diode 101 responsively to the analog-to-digital converter 99. The light 103 is directed to fiberoptic element 105 by suitable optical elements (not shown).

First Alternate Embodiment

Reverting to FIG. 3, the assemblies 41 are typically used as mapping electrodes. However, a portion of them may be employed as electrodes for impedance measurements in order to determine the location of the distal portion of the catheter 37. Suitable impedance-based tracking systems are described in commonly assigned U.S. Patent Application Publication Nos. 2007/0016007 and 2007/0060832, whose disclosures are incorporated herein by reference.

Second Alternate Embodiment

Figure 6:
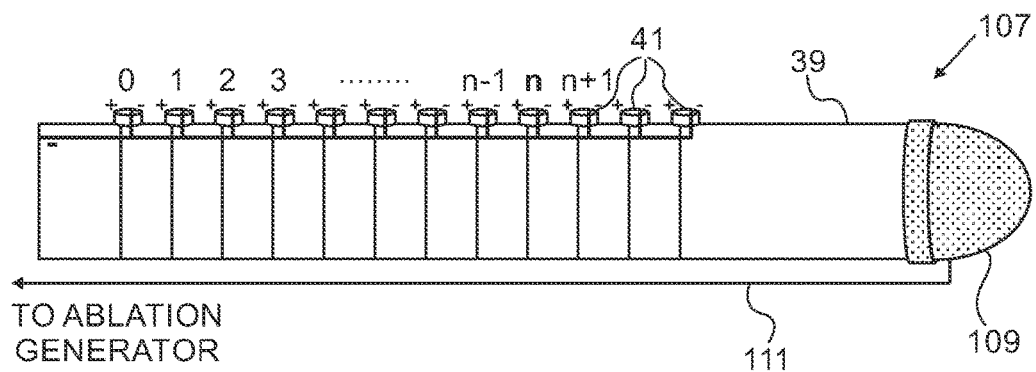
FIG. 6 is a schematic diagram of a portion of a catheter, in accordance with an alternate embodiment of the invention.

Conventional elements may be mounted on a catheter that is constructed according to the previous embodiments. Reference is now made to FIG. 6, which is a schematic diagram of a fiberoptic catheter 107, in accordance with an alternate embodiment of the invention. The catheter 107 has the same general construction as the catheter 37 (FIG. 2). However, an ablation electrode 109 is now mounted on the distal end of the fiberoptic cable 39, and may be connected to a power source (not shown) by a wire 111.

Third Alternate Embodiment

Figure 7:
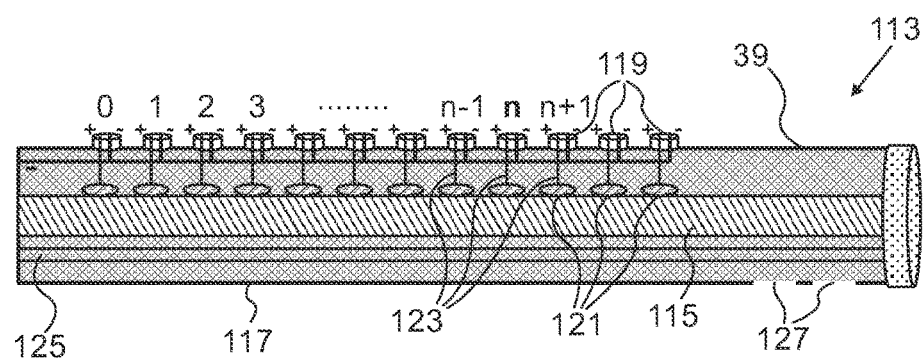
FIG. 7 is a schematic diagram of a portion of a catheter, in accordance with an alternate embodiment of the invention.

Reference is now made to FIG. 7, which is a schematic diagram of a fiberoptic catheter 113, in accordance with an alternate embodiment of the invention. In this embodiment, a fiberoptic waveguide 115 is coaxially disposed within the lumen of a probe 117. Electrode assemblies 119 on the exterior of the probe 117 have positive and negative electrodes as described in the previous embodiments. The assemblies 119 are not integral with LEDs 121, but are spaced apart from the LEDs 121 at a distance measured from the exterior of the waveguide 115 to the outer wall of the probe 117. The assemblies 119 are connected to the LEDs 121 by conductors 123. This arrangement allows for other components, e.g., electrical or hydraulic conduits 125 to be included within the probe 117. The conduits 125 may communicate with other components (not shown) that may be disposed on or within the probe 117. Additionally or alternatively, the conduits 125 may conduct irrigation fluid to an operative site through exit pores 127.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
    a probe adapted to be percutaneously inserted by an operator through a living subject's vascular system into a chamber or vascular structure of a heart, the probe comprising:
        a fiberoptic waveguide comprising a proximal portion and distal portion, the proximal portion configured to be connectable to a console located externally to the patient; and
        a plurality of electro-optical assemblies, each optically coupled to the waveguide at a respective discrete location along the distal portion;
    wherein each one of the plurality of electro-optical assemblies comprises:
        a first electrode having a first polarity,
        a second electrode;
        a light-emitting diode linked to the first electrode; and
        a conductive ring connected to the first electrode;
    wherein the first electrode and conductive ring of each one of the plurality of electro-optical assemblies are configured to detect electrical potentials at the respective discrete location;
    wherein the second electrodes of each one of the electro-optical assemblies have the same polarity and are connected in common by a common connection;
    wherein each light-emitting diode of the plurality of electro-optical assemblies comprises light-emitting diode optics configured for communicating optical signals to the console responsively to an electrical potential between the respective first and second electrodes by illuminating the waveguide at a respective wavelength unique to each light emitting diode.

2. The apparatus according to claim 1, wherein the electro-optical assemblies further comprise respective transmissive optical elements, and the waveguide comprises a core and a cladding layer formed coaxially about the core, the cladding layer having optically transparent gaps formed therein, the transmissive optical elements overlying the gaps.

3. The apparatus according to claim 1, further comprising an optic terminator disposed in the waveguide.

4. The apparatus according to claim 1, wherein the electro-optical assemblies further comprise an analog-to-digital converter linked to the first electrode and to the light-emitting diode.

5. The apparatus according to claim 4, wherein the electro-optical assemblies further comprise an amplifier linked to the first electrode and to the analog-to-digital converter.

6. The apparatus according to claim 4, further comprising a third electrode and a wire connected to the third electrode for exchanging electrical signals between the third electrode and a source.

7. The apparatus according to claim 1, further comprising a probe, wherein the waveguide is coaxially disposed within the probe.

8. The apparatus according to claim 7, wherein the first electrode and the second electrode are spaced apart from the light-emitting diode at a distance measured from an exterior of the waveguide to an outer wall of the probe.

9. The apparatus according to claim 1, further comprising:
an optical receiver coupled to the proximal portion of the waveguide, the optical receiver configured to discriminate the optical signals produced by each one of the plurality of electro-optical assemblies; and
the console located externally to the patient;
wherein the optical signals are converted to electrical signals and processed in the console.

10. A method, comprising the steps of:
inserting a probe into a heart of a living subject to contact a target, the probe comprising a proximal portion and a distal portion;
connecting a proximal portion of the probe to a console, the console located externally to the living subject, wherein the probe comprises a fiberoptic waveguide and a plurality of electro-optical assemblies, each optically coupled to the waveguide at a respective discrete location along the distal portion, each one of the plurality of electro-optical assemblies comprising:
a first electrode having a first polarity,
a second electrode;
a light-emitting diode linked to the first electrode; and
a conductive ring connected to the first electrode;
each one of the first electrodes and conductive ring of each one of the plurality of electro-optical assemblies detecting at the respective discrete location respective electrical potentials at the target; and
each one of the light-emitting diodes comprising light-emitting diode optics to communicate optical signals to the console by illuminating the waveguide responsively to the respective electrical potentials at a respective wavelength unique with respect to the other light emitting diodes;
wherein the second electrodes of each one of the electro-optical assemblies have the same polarity and are connected in common by a common connection.

11. The method according to claim 10, wherein the electro-optical assemblies comprise respective transmissive optical elements, and the waveguide comprises a core and a cladding layer formed coaxially about the core, the cladding layer having optically transparent gaps formed therein, the transmissive optical elements overlying the gaps.

12. The method according to claim 10, the probe further comprising an optic terminator disposed in the waveguide.

13. The method according to claim 10, wherein the electro-optical assemblies further comprise an analog-to-digital converter linked to the first electrode and to the light-emitting diode thereof.

14. The method according to claim 13 wherein the electro-optical assemblies further comprise an amplifier linked to the first electrode and to the analog-to-digital converter.

15. The method according to claim 10, wherein the first electrode and the second electrode are spaced apart from the light-emitting diode at a distance measured from an exterior of the waveguide to an outer wall of the probe.

16. The method according to claim 10, further comprising:
each one of the plurality of electro-optical assemblies detecting respective electrical potentials at the respective discrete location and communicating an optical signal to an optical receiver responsively to the respective electrical potentials by illuminating the waveguide at the respective wavelength;
discriminating the optical signals produced by each one of the plurality of electro-optical assemblies and converting the optical signals into electrical signals; and
processing the electrical signals in the console.

* * * * *